(12) United States Patent
Gubich et al.

(10) Patent No.: US 11,013,483 B2
(45) Date of Patent: May 25, 2021

(54) IMAGING CAPSULE LOCATION DETECTION

(71) Applicant: CHECK-CAP LTD., Isfiya (IL)

(72) Inventors: Dmitry Gubich, Kiryat Motzkin (IL); Avner Elgali, Kochav Yair (IL); Yoav Kimchy, Haifa (IL)

(73) Assignee: CHECK-CAP LTD, Isfiya (IL)

( * ) Notice: Subject to any disclaimer, the term of this patent is extended or adjusted under 35 U.S.C. 154(b) by 466 days.

(21) Appl. No.: 15/572,790

(22) PCT Filed: May 1, 2016

(86) PCT No.: PCT/IL2016/050447
§ 371 (c)(1),
(2) Date: Nov. 9, 2017

(87) PCT Pub. No.: WO2016/181380
PCT Pub. Date: Nov. 17, 2016

(65) Prior Publication Data
US 2018/0153497 A1    Jun. 7, 2018

Related U.S. Application Data

(60) Provisional application No. 62/159,284, filed on May 10, 2015.

(51) Int. Cl.
*A61B 6/00* (2006.01)
*A61B 5/07* (2006.01)
(Continued)

(52) U.S. Cl.
CPC .......... *A61B 6/541* (2013.01); *A61B 1/00147* (2013.01); *A61B 1/041* (2013.01); *A61B 1/043* (2013.01); *A61B 1/2736* (2013.01); *A61B 5/036* (2013.01); *A61B 5/065* (2013.01); *A61B 5/066* (2013.01); *A61B 5/073* (2013.01); *A61B 6/4057* (2013.01); *A61B 6/4258* (2013.01);
(Continued)

(58) Field of Classification Search
CPC ......... A61B 1/041; A61B 5/065; A61B 5/073; A61B 5/036; A61B 6/4258
See application file for complete search history.

(56) References Cited

U.S. PATENT DOCUMENTS 5,573,007 A * 11/1996 Bobo, Sr. ............. A61B 5/0215
600/561
2004/0102733 A1 * 5/2004 Naimark ................ A61B 5/145
604/65
(Continued)

FOREIGN PATENT DOCUMENTS

| WO | 20060021932 A1 | 3/2006 |
| WO | 2008012700 A1 | 1/2008 |
| WO | 20090063377 A1 | 5/2009 |

*Primary Examiner* — Jason M Ip
(74) *Attorney, Agent, or Firm* — Soroker Agmon Nordman

(57) ABSTRACT

An imaging capsule configured to be swallowed to scan the gastrointestinal tract of a person from the inside, including a radiation source providing X-Ray and gamma radiation for scanning the gastrointestinal tract, a pressure sensor for measuring the internal pressure in the imaging capsule; and wherein the imaging capsule is configured to control the emission of radiation from within the imaging capsule responsive to the measurements of the pressure sensor.

20 Claims, 5 Drawing Sheets

(51) Int. Cl.
*A61B 5/03* (2006.01)
*A61B 1/00* (2006.01)
*A61B 1/04* (2006.01)
*A61B 1/273* (2006.01)
*A61B 5/06* (2006.01)

(52) U.S. Cl.
CPC .......... *A61B 6/4405* (2013.01); *A61B 6/4417* (2013.01); *A61B 6/4452* (2013.01); *A61B 6/50* (2013.01); *A61B 6/56* (2013.01)

(56) References Cited

U.S. PATENT DOCUMENTS

| | | | |
|---|---|---|---|
| 2007/0161885 A1* | 7/2007 | Kimchy | A61B 5/073 600/407 |
| 2009/0163771 A1* | 6/2009 | Kimoto | A61B 1/00016 600/118 |
| 2014/0081360 A1* | 3/2014 | Ben-Yehuda | A61N 5/0603 607/92 |
| 2015/0011874 A1* | 1/2015 | Amoako-Tuffour | A61B 10/04 600/424 |

* cited by examiner

IMAGING CAPSULE LOCATION DETECTION

RELATED APPLICATIONS

This application claims priority under 35 U.S.C. 120 from U.S. provisional application No. 62/159,284 dated May 10, 2015, the disclosure of which is incorporated herein by reference.

FIELD OF THE DISCLOSURE

The present disclosure relates generally to the detection of pre-cancerous and cancerous tissue in the colon using a swallowable capsule and more specifically to detection of the location of the capsule within an examined subject.

BACKGROUND OF THE DISCLOSURE

One method for examining the gastrointestinal tract for the existence of polyps and other clinically relevant features that may provide an indication regarding the potential of cancer is performed by swallowing an imaging capsule that travels through the gastrointestinal tract and views the patient's situation from within. In a typical case the trip can take between 24-48 hours after, after which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radio-isotope that emits X-rays and/or Gamma rays. The radiation typically may be collimated to allow it to be controllably directed toward a specific area during the imaging process. In an exemplary case the imaging capsule is designed to measure X-Ray fluorescence and/or Compton back-scattering and transmit the measurements (e.g. count rate, particle energy) to an external analysis device, for example a transceiver worn by the patient and/or a computer or other dedicated instruments.

U.S. Pat. No. 7,787,926 dated Aug. 31, 2010 and U.S. Pat. No. 9,037,219 dated May 19, 2015 both by the current applicant, the disclosures of which are incorporated herein by reference, describe details related to the manufacture and use of such an imaging capsule.

It is desirable to minimize the amount of radiation released inside the patient's body and to optimize the energy expenditure by the imaging capsule. Therefore it is desirable to block the release of radiation until reaching the location that needs to be examined, for example once reaching the beginning of the Colon, e.g. entering the Cecum. Accordingly, it would be desirable that the imaging capsule have the ability to identify in which organ it is located and especially when it reaches the Colon, so that the imaging capsule can limit the use of energy and the release of radiation to these areas.

SUMMARY OF THE DISCLOSURE

An aspect of an embodiment of the disclosure, relates to an imaging, capsule for scanning inside the gastrointestinal tract to detect abnormalities. The imaging capsule includes a pressure sensor to measure pressure as it traverses the gastrointestinal tract. Based on the pressure measurements the imaging capsule determines its location within the gastrointestinal tract, for example in which organ it is located. The imaging capsule can be preconfigured or instructed in real-time to start scanning at specific locations and stop scanning at other locations. In some embodiments of the disclosure, the determination is made by a controller in the imaging capsule. Alternatively, the capsule may transmit measurements to an external device or computer for analysis and the external device or computer provides instructions to the imaging capsule.

In an exemplary embodiment of the disclosure, the determination is based on pressure measurements resulting from gas diffusing into the imaging, capsule as it traverses the gastrointestinal tract. Alternatively or additionally, the pressure measurements are the result of hydrostatic forces applied by the contents surrounding the imaging capsule and/or forces applied by the muscles of the organ surrounding the imaging capsule (e.g. colon muscles).

There is thus provided according to an exemplary embodiment of the disclosure, an imaging capsule configured to be swallowed to scan the gastrointestinal tract of a person from the inside, comprising:

a radiation source providing X-Ray and gamma radiation for scanning the gastrointestinal tract;

a pressure sensor for measuring the internal pressure in the imaging capsule; and wherein said imaging capsule is configured to control the emission of radiation from within the imaging capsule responsive to the measurements of the pressure sensor.

In an exemplary embodiment of the disclosure, the imaging capsule further comprises a controller that records the measurements of the pressure sensor, analyzes them and determines in which organ of the person the imaging capsule is located based on the measurements. Optionally, the imaging, capsule further comprises a transceiver for communicating with an external device. In an exemplary embodiment of the disclosure, the imaging capsule provides the measurements of the pressure sensor to an external device to determine the location of the imaging capsule and instruct the imaging capsule if to commence or cease scanning the gastrointestinal tract. Optionally, the imaging capsule further comprises an encasement made from a rigid material and windows covered by a softer material that is pushed in or pushed out relative to the encasement in response to a difference in pressure inside the capsule and outside the capsule. In an exemplary embodiment of the disclosure, the rigid material and or the softer material are penetrable by gas molecules. Optionally, the imaging capsule is configured to commence scanning upon entering the colon. In an exemplary embodiment of the disclosure, the imaging capsule is configured to cease scanning, upon exiting the colon. Alternatively or additionally, the imaging capsule is configured to commence scanning after a preselected amount of time from entering a specific organ. In an exemplary embodiment of the disclosure, the imaging capsule is configured to scan when identifying extreme fluctuations or specific behavior in the pressure measurements.

There is further provided according to an exemplary embodiment of the disclosure, a method of controlling the release of radiation by an imaging capsule, comprising:

introducing, into the gastrointestinal tract an imaging capsule with a controllable radiation source that provides X-ray and gamma radiation for scanning the gastrointestinal tract from within;

measuring the pressure within the imaging capsule as it traverses the gastrointestinal tract;

analyzing the pressure measurements to determine the current location of the imaging capsule;

instructing the imaging capsule to commence or cease releasing radiation responsive to the analysis of the pressure measurements.

In an exemplary embodiment of the disclosure, the imaging capsule includes a controller that records the measurements of the pressure sensor and analyzes the measurements to determine in which organ of the person the imaging capsule is located based on the measurements. Optionally, the imaging capsule includes a transceiver for communicating with an external device. In an exemplary embodiment of the disclosure, the imaging capsule provides the measurements of the pressure sensor to an external device to determine the location of the imaging capsule and instruct the imaging capsule if to commence or cease scanning the gastrointestinal tract. Optionally, the imaging capsule includes an encasement made from a rigid material and windows covered by a softer material that is pushed in or pushed out relative to the encasement in response to a difference in pressure inside the capsule and outside the capsule. In an exemplary embodiment of the disclosure, the rigid material and/or the softer material are penetrable by gas molecules. Optionally, the imaging capsule is configured to commence scanning upon entering the colon. In an exemplary embodiment of the disclosure, the imaging capsule is configured to cease scanning upon exiting the colon. Alternatively or additionally, the imaging capsule is configured to commence scanning alter a preselected amount of time from entering a specific organ. In an exemplary embodiment of the disclosure, the imaging capsule is configured to scan when identifying extreme fluctuations or specific behavior in the pressure measurements.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
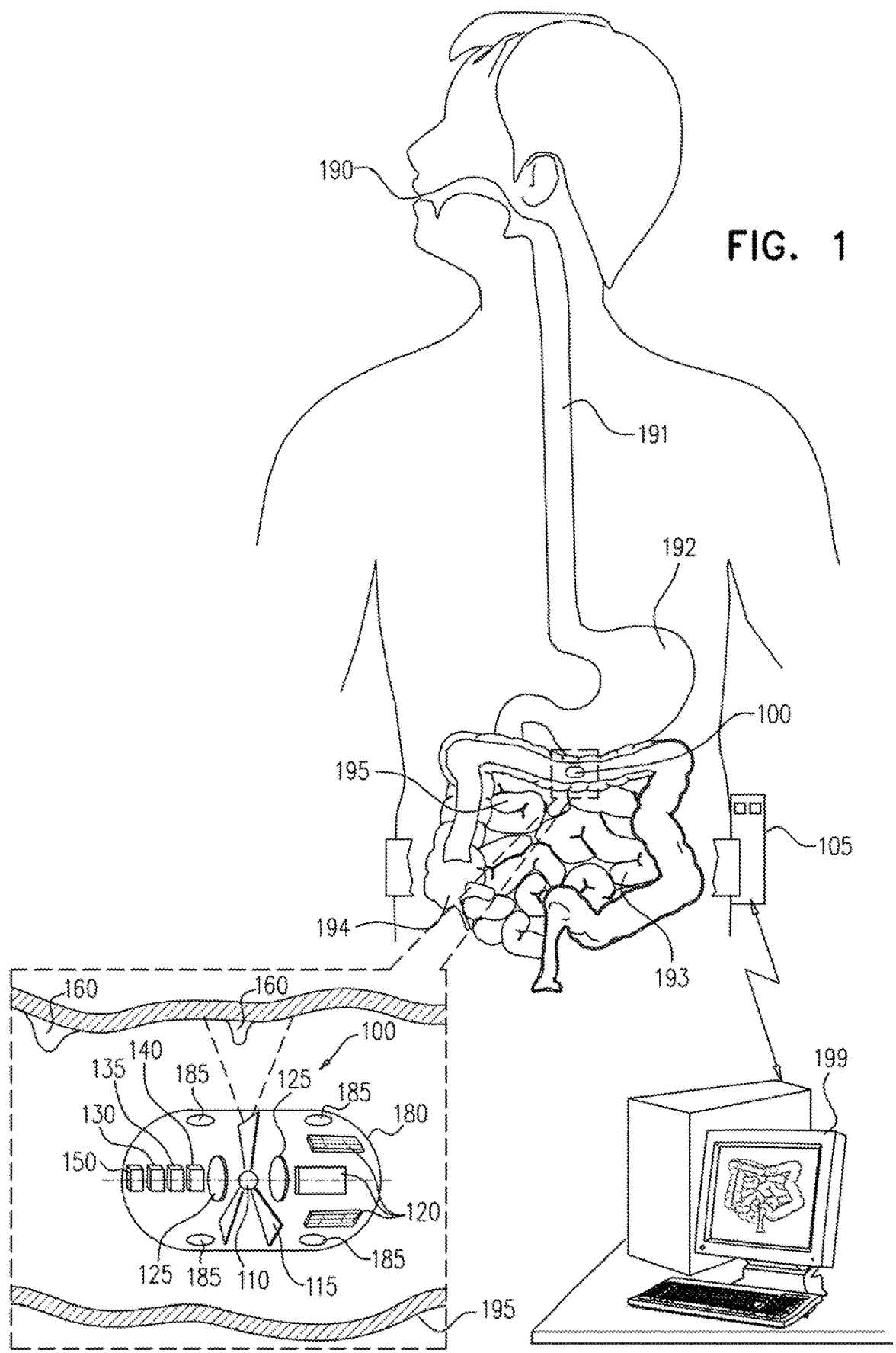
FIG. 1 is a schematic illustration of an imaging capsule deployed in a patient's colon, according to an exemplary embodiment of the disclosure.

FIG. 1 is a schematic illustration of an imaging capsule 100 deployed in a patients colon 195, according, to an exemplary embodiment of the disclosure. Optionally, the patient first swallows a radio opaque contrast agent solution (e.g. based on Barium or Iodine). The radio opaque contrast agent solution mixes with the content of the gastrointestinal tract to increase the accuracy in detecting cancerous tissue based on measurements taken from inside the patient's body. After swallowing the radio opaque contrast agent solution the patient swallows the imaging capsule 100. In an exemplary embodiment of the disclosure, the imaging capsule travels through the patient's mouth 190, esophagus 191, stomach 192, small intestine 193 and then enters the cecum 194, which is the beginning of the colon 195. In an exemplary embodiment of the disclosure, the imaging capsule 100 identifies its location, for example that it has entered the colon 195 and then the imaging; capsule will begin scanning by releasing radiation to form images from inside the colon 195. Optionally, the imaging capsule can release radiation at any location along the gastrointestinal tract, for example in the small intestine 193 or in the stomach 192.

In some embodiments of the disclosure, instead of storing the measurements and analyzing them internally the measurements are provided to an external transceiver 105 that is worn by the user and stored for analysis, for example stored on a memory card (e.g. SD card) that can be extracted and read on a computer 199. Alternatively or additionally, the external transceiver 105 stores and analyzes the measurements. Further alternatively or additionally, the measurements may be transmitted directly from the imaging capsule 100 to the computer 199 or transmitted to the external transceiver 105 and then provided to the computer 199 in real-time.

In an exemplary embodiment of the disclosure, imaging capsule 100 comprises an encasement 180 shaped as an elongated cylinder with an elongated axis and having flat or spherically shaped ends. Alternatively, other shapes may be used, for example a parallelepiped having flat ends, pyramid shaped ends or other shapes. In an exemplary embodiment of the disclosure, imaging capsule 100 includes a radiation source 110 that emits X-Ray or gamma radiation and is positioned at the center of a collimator 115 (e.g. a circular/cylindrical collimator) to control the direction of emission of radiation from the radiation source 110. In an exemplary embodiment of the disclosure, the imaging capsule controls the release of radiation through the collimators, so that the imaging capsule can block the emission of radiation or unblock the emission of radiation in addition to controlling its direction. Optionally, the radiation source is also located between two radiation blocking disks 125 (e.g. cylindrical tungsten disks) to prevent emission of radiation from the upper and lower ends of the imaging capsule 100.

In an exemplary embodiment of the disclosure, the imaging capsule 100 further includes any of the following: one or more radiation detectors 120, a power source 150 (e.g. a battery), a controller 130 optionally having a processor and memory to analyze the measurements and provide instructions, a pressure sensor 135 and a transceiver 140 for communicating with an external transceiver 105 or computer 199 to receive instructions and provide measurements/images.

In an exemplary embodiment of the disclosure, the elements of the imaging capsule 100 (e.g. 120, 130, 135 140, 150) are connected electronically and/or physically to enable the imaging capsule 100 to function correctly, for example the detectors 120 detect the energy levels of particles emitted responsive to radiation emitted by the radiation source and provide the information to controller 130 and/or transceiver 140.

In an exemplary embodiment of the disclosure, pressure sensor 135 may be a high sensitivity pressure sensor such as LPS25H from STmicrosystems or a similar element.

In an exemplary embodiment of the disclosure, the colon 195 may include cancerous or non-cancerous polyps/tumors 160 for example as shown in FIG. 1. Optionally, as imaging, capsule 100 traverses the colon it radiates the inner walls of the colon 195 with X-Ray and gamma radiation. In response detectors 120 of imaging capsule 100 detect particles (e.g. photons, electrons) responding to the emitted radiation. Optionally, imaging capsule 100 forms a count for each energy level representing the number of particles having the specific energy level resulting from Compton backscattering and X-Ray fluorescence. These measurements are then analyzed to form images of the insides of the colon 195.

In an exemplary embodiment of the disclosure, encasement 180 is mostly made up from a rigid material such as Polycarbonate with windows 185 optionally covered by a softer material, for example silicon or thermoplastic elastomers (TPE), adhering to the rigid material. Optionally, the softer material is pushed in or pushed out in response to a difference in the pressure inside the capsule relative to the pressure outside the capsule in the different organs of the patient (e.g. stomach 192, small intestine 193 or colon 195). Optionally, when the softer material is pushed inward the volume of the imaging capsule 100 decreases and the pressure increases. In an exemplary embodiment of the disclosure, pressure sensor 135 identifies the change in the pressure from inside the imaging capsule 100 and uses it to determine the location of the capsule (e.g. in which organ it is currently located or if it is at the beginning or end of the organ).

Figure 2:
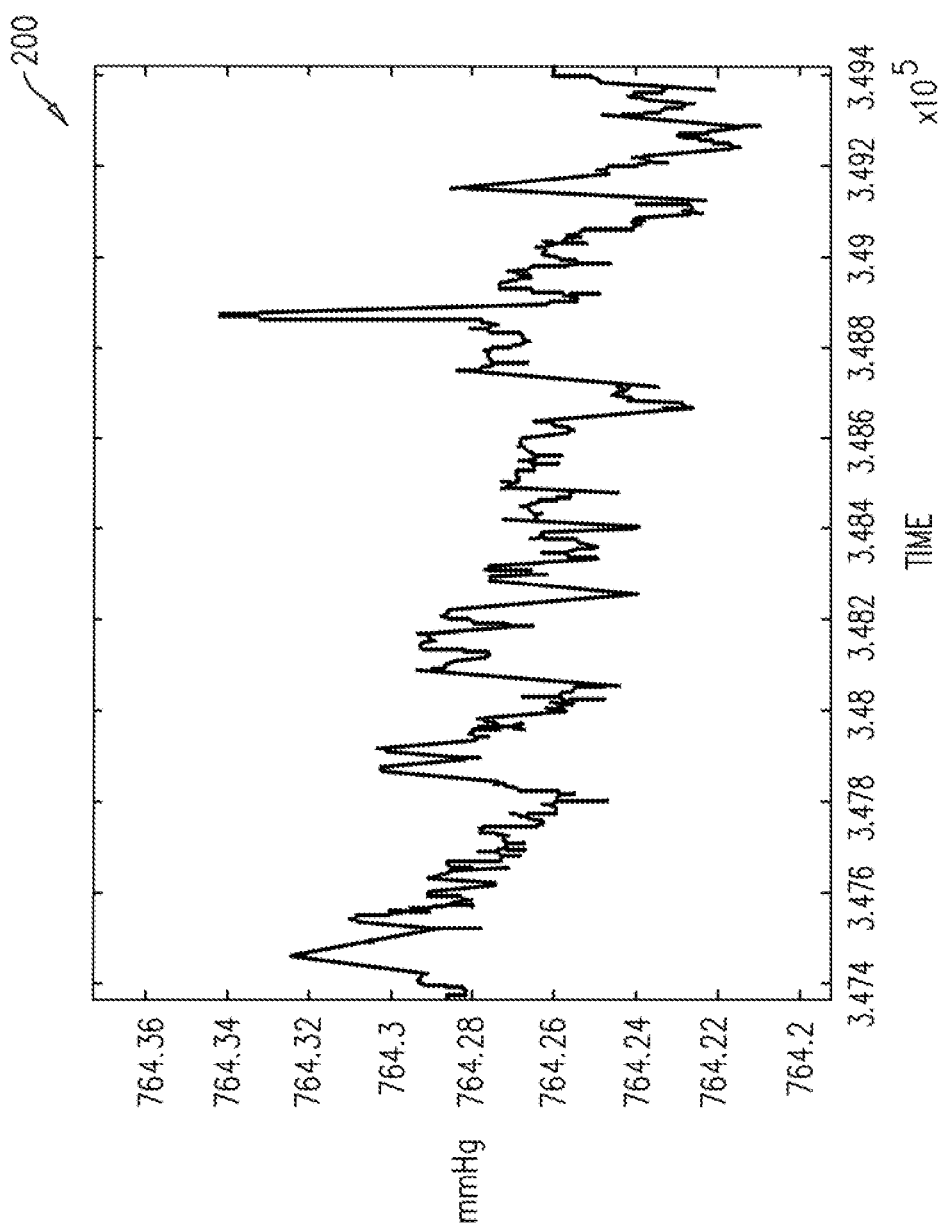
FIG. 2 is a schematic illustration of a graph of typical pressure waves in the small intestine, according to an exemplary embodiment of the disclosure.
Figure 3:
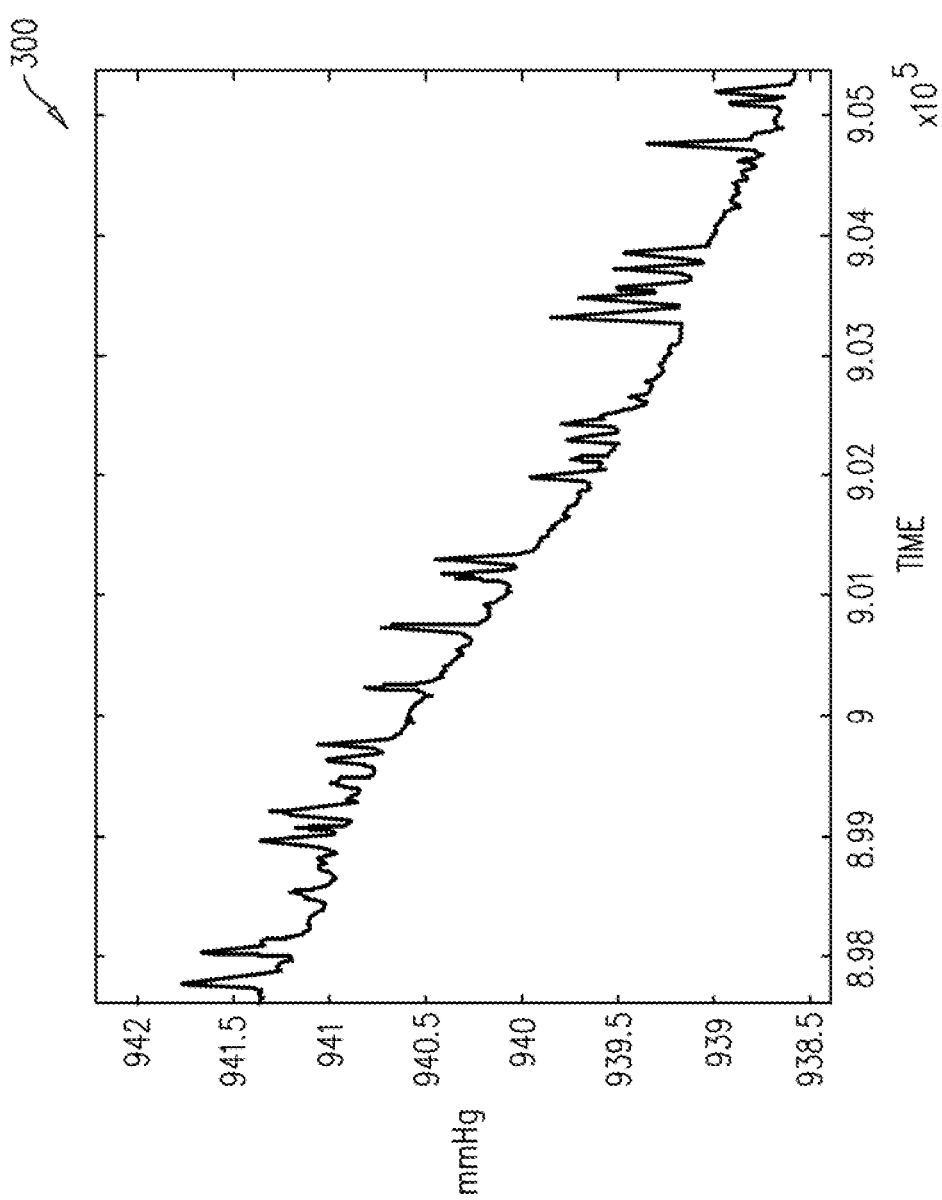
FIG. 3 is a schematic illustration of a graph of typical pressure waves in the colon, according to an exemplary embodiment of the disclosure.

In an exemplary embodiment of the disclosure, the pressure measured by pressure sensor 135 is due to forces applied by the muscles of the small intestine 193, colon 195 and/or other organ. Alternatively or additionally, the pressure measured is due to hydrostatic pressures in each organ, for example from the content and pressure on the content. Optionally, the hydrostatic pressure in the colon 195 causes pressure waves with a duration of a few seconds to a few tens of seconds in contrast to a different timing in the small intestine 193. In an exemplary embodiment of the disclosure, pressure waves in the small intestine 193 are typically of the order of 1-20 mmHg in contrast to pressure waves in the colon, which are typically of the order of 20-100 mmHg. Optionally, the difference in hydrostatic pressure is used to differentiate between the locations of the imaging capsule 100. In an exemplary embodiment of the disclosure, the frequency of the pressure waves is used to distinguish between the small intestine 193, the colon 195 and other organs, for example pressure waves in the small intestine 193 tend to be regular with a typical time interval of 15-20 seconds between the pressure waves. In contrast in the colon the interval between pressure waves tends to be random (e.g. irregular) with typical time intervals of a few minutes to a few hours between pressure waves. FIG. 2 is a schematic graph 200 of typical pressure waves in the small intestine 193 and FIG. 3 is a schematic graph 300 of typical pressure waves in the colon 195.

In an exemplary embodiment of the disclosure, gases can penetrate the encasement 180 of imaging capsule 100. Optionally, the gases penetrates by diffusion into the imaging capsule 100 at a rate that is dependent on the material of the encasement 180. For example a rigid material such as polycarbonate enables slower diffusion than silicon.

In an exemplary embodiment of the disclosure, the gas diffusion causes the internal pressure of the imaging capsule 100 to gradually rise with the hydrostatic pressure and muscle pressure causing relatively small fluctuations around the internal pressure due to the diffusion. Initially, the pressure inside the imaging capsule 100 is about 1 atmosphere (760 mmHg) and the pressure increases while traversing the gastrointestinal tract. Optionally, the gastrointestinal tract includes $CO_2$, Methane ($CH_4$), $H_2$ and other gases which are generally dissolved or generated by the contents in the colon 195. The contents of the colon 195 include a large number of bacteria of different types and species that release $H_2$, Methane, $CO_2$ and other gases during their metabolic processes. The bacteria reside mainly in the colon and much less in the small intestine 193. Therefore, the presence of these gases is mainly confined to the colon 195. Optionally, the pressure in the colon 195 is about 100-250 mmHg greater than 1 atmosphere, depending on the size, weight and posture of the patient. This difference in pressure induces the gases to diffuse into the imaging capsule 100 at a faster rate than in the small intestine 193. In an exemplary embodiment of the disclosure, diffusion starts once the imaging capsule 100 is swallowed and increases from the stomach 192 to the small intestine 193 and further increases in the cecum 194 and colon 195. Generally, the diffusion is relatively limited the stomach 192 and the small intestine 193 but, increases substantially when the imaging capsule 100 enters the colon 195 due to the presence of bacteria in the colon 195. Optionally, in the small intestine 193 the imaging capsule 100 is engulfed by small tissue with almost no content in contact with the capsule, therefore only small amounts of gas molecules diffuse through the imaging capsule walls. However when the imaging capsule 100 enters the cecum 194 a large amount of content with a lot of dissolved gas is in contact with the imaging capsule 100 and the influx of gas molecules into the imaging capsule 100 is increased sharply to equalize the pressure inside the imaging capsule 100 with the surrounding content.

Figure 4:
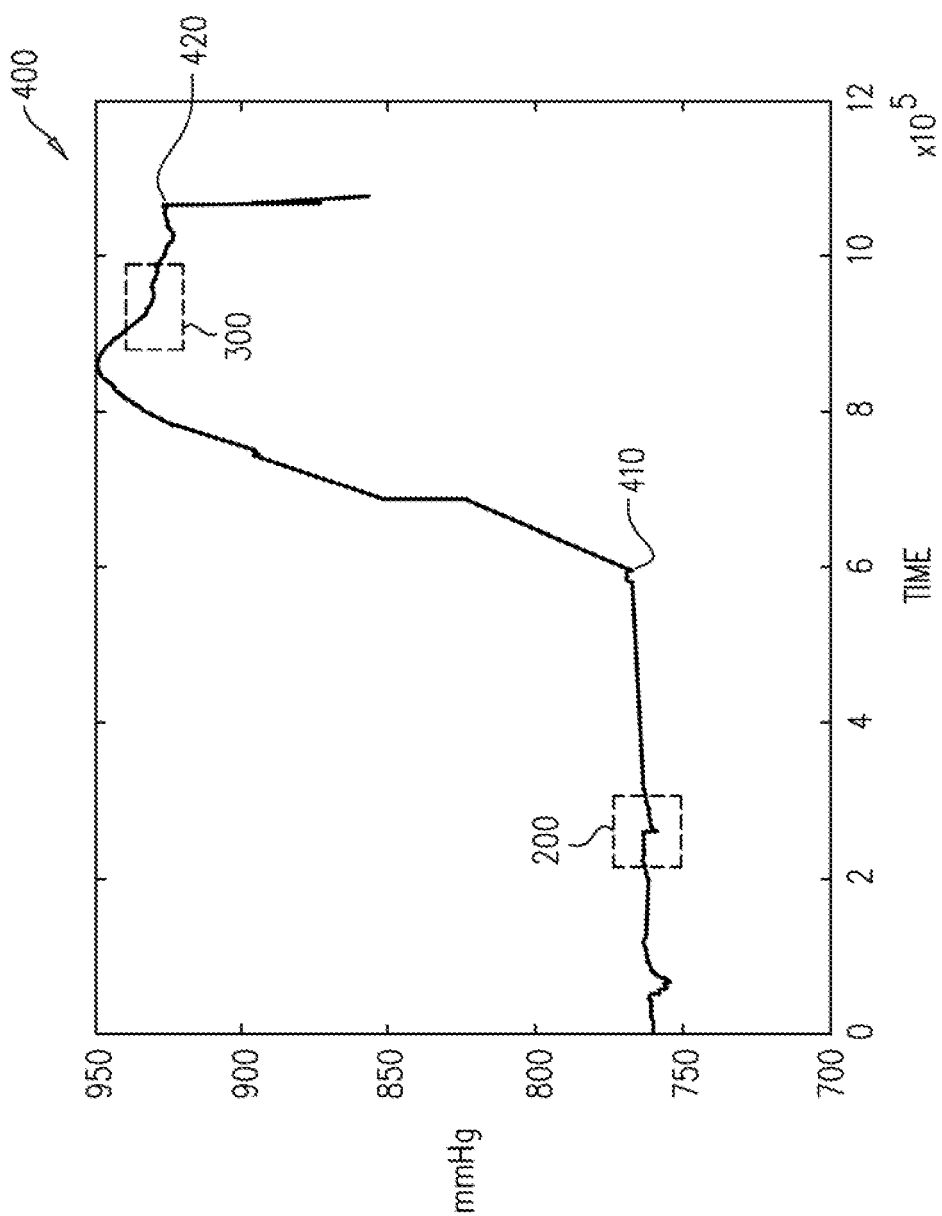
FIG. 4 is a schematic illustration of a graph showing a typical increase in internal pressure over time due to gas diffusion, according to an exemplary embodiment of the disclosure.
Figure 5:
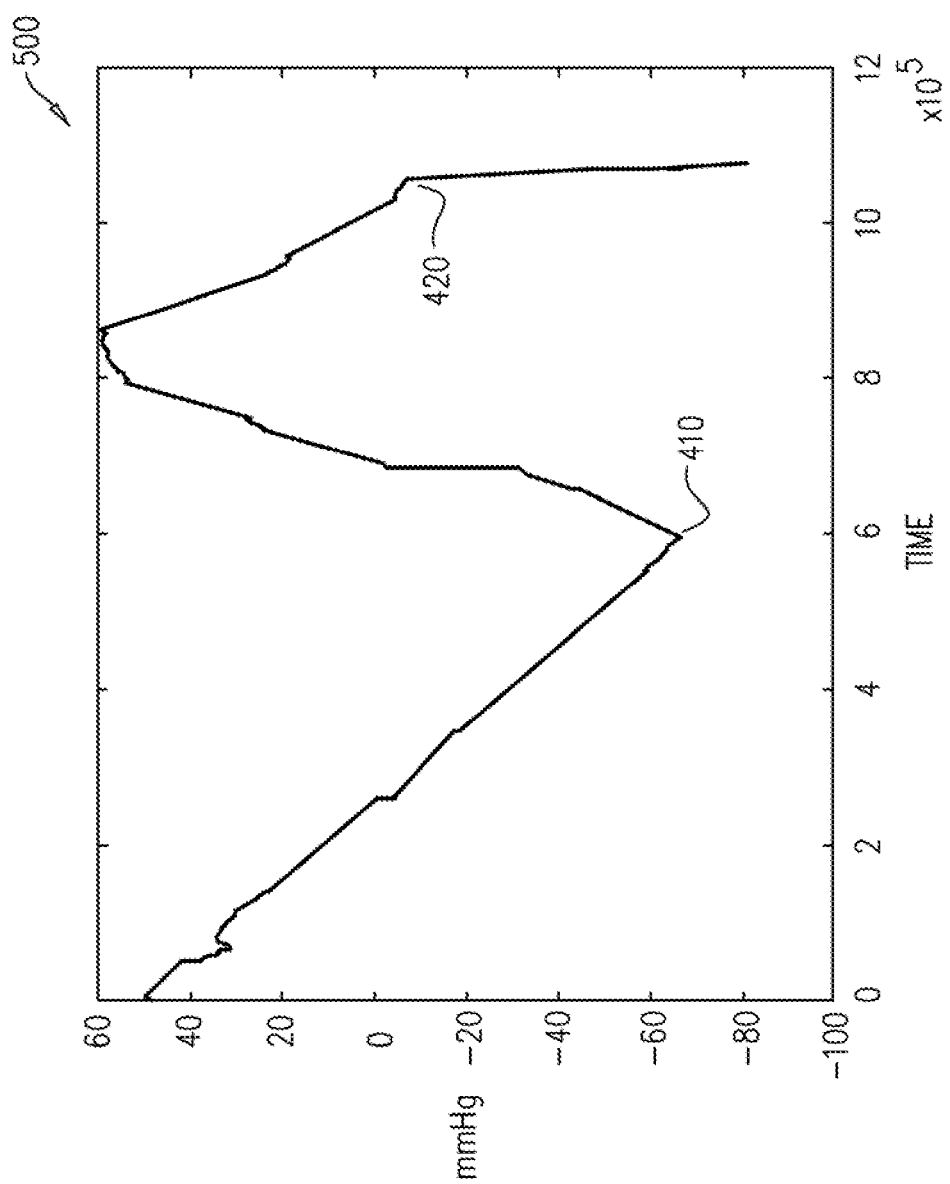
FIG. 5 is a schematic illustration of a graph of a simple de-trend of the graph showing a typical increase in internal pressure over time due to gas diffusion, according to an exemplary embodiment of the disclosure.

In an exemplary embodiment of the disclosure, pressure sensor 135 records an increase in the pressure as more gas enters the capsule by diffusion. FIG. 4 is a schematic illustration of a graph 400 showing a typical increase in internal pressure over time due to gas diffusion. Optionally, graph 200 is an enlarged view of the earlier stage in graph 400, depicting fluctuations of pressure of the imaging capsule 100 in the small intestine 193 and graph 300 is an enlarged view of a later stage of graph 400 depicting the pressure in the imaging capsule 100 in the colon. FIG. 5 is a schematic illustration of a graph 500 showing a simple de-trend of the graph in FIG. 4 emphasizing the inflection points of internal capsule pressure, for example point 410 as the imaging capsule 100 enters the colon 195 and point 420 when the imaging capsule 100 exits the anus.

In an exemplary embodiment of the disclosure, based on the explanation above controller 130 determines the location of the imaging capsule 100, for example if it is in, the stomach 192, the small intestine 193, the colon 195 or in the beginning or end of each organ. Alternatively, the recorded information e.g. pressure measurements) are transmitted to external transceiver 105 and analyzed there or transmitted from there to computer 199 for analysis. Optionally, the analysis is performed in real-time so that scanning may be started or stopped in response to the measurements and determinations made based on the analysis (e.g. when entering the colon or exiting the colon or rectum). In an exemplary embodiment of the disclosure, external transceiver 105 or computer 199 may notify the capsule to commence or cease radiating based on the location of the imaging capsule 100 determined from the analysis.

In an exemplary embodiment of the disclosure, analysis of the pressure measurements is performed continuously or periodically. Optionally, during analysis the previous calculations are verified based on the new measurements to differentiate between fluctuations inside a specific organ and transition into a different organ. Optionally, imaging capsule 100 may start radiating at a preselected time after entering a specific organ, for example a few hours after entering the small intestine 193 before it is expected to enter the colon, to be sure to scan the cecum 194 and or the entire colon 195. Alternatively or additionally, the imaging capsule 100 may be configured to start scanning with radiation every time there is an extreme fluctuation in the pressure measurements or a specific behavior, for example to catch transitions from one organ to another.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present invention is not limited to what has been particularly shown and described hereinabove. Rather the scope of the present invention is defined only by the claims, which follow.

We claim:

1. An imaging capsule configured to be swallowed to scan a gastrointestinal tract of a person from the inside of the person, comprising:
   a radiation source providing X-ray and gamma radiation for scanning the gastrointestinal tract;
   a pressure sensor configured to measure an internal pressure in the imaging capsule reflecting a magnitude of hydrostatic pressure within the imaging capsule due to gas diffusion from outside the imaging capsule into the imaging capsule;
   a controller configured to identify fluctuations in the magnitude of hydrostatic pressure due to gas diffusion, analyze the internal pressure reflecting the hydrostatic pressure and the identified fluctuations to determine a location of the imaging capsule inside the gastrointestinal tract; and
   wherein said imaging capsule is configured to control the emission of the radiation from within the imaging capsule responsive to the determined location.

2. An imaging capsule according to claim 1, wherein the determining the location includes identifying in which organ of the person the imaging capsule is located.

3. An imaging capsule according to claim 1, further comprising a transceiver for communicating with an external device.

4. An imaging capsule according to claim 3, wherein the imaging capsule provides the measurements of the pressure sensor to the external device to determine the location of the imaging capsule and to instruct the imaging capsule whether to commence or cease scanning the gastrointestinal tract.

5. An imaging capsule according to claim 1, further comprising an encasement made from a rigid material and windows covered by a softer material that is pushed in or pushed out relative to the encasement in response to a difference in pressure inside the imaging capsule and outside the imaging capsule.

6. An imaging capsule according to claim 5, wherein the rigid material and/or the softer material are penetrable by gas molecules.

7. An imaging capsule according to claim 1, wherein the imaging capsule is configured to commence scanning upon entering the colon.

8. An imaging capsule according to claim 1, wherein the imaging capsule is configured to cease scanning upon exiting the colon.

9. An imaging capsule according to claim 1, wherein the imaging capsule is configured to commence scanning after a preselected amount of time after entering a specific organ.

10. An imaging capsule according to claim 1, wherein the imaging capsule is configured to scan when identifying the fluctuations or a specific behavior in the pressure measurements.

11. A method of controlling a release of radiation by an imaging capsule, comprising:
    introducing into a gastrointestinal tract an imaging capsule with a controlled radiation source that provides X-ray and gamma radiation for scanning the gastrointestinal tract from within;
    measuring an internal pressure within the imaging capsule as it traverses the gastrointestinal tract; wherein the internal pressure reflects a magnitude of hydrostatic pressure within the imaging capsule due to gas diffusion from outside the imaging capsule into the imaging capsule;
    identifying fluctuations in the hydrostatic pressure due to gas diffusion;
    analyzing the internal pressure reflecting the hydrostatic pressure and the identified fluctuations to determine a current location of the imaging capsule;
    instructing the imaging capsule to commence or cease releasing the radiation responsive to the determined location.

12. A method according to claim 11, wherein the determining the location includes identifying in which organ of the person the imaging capsule is located.

13. A method according to claim 11, wherein the imaging capsule includes a transceiver for communicating with an external device.

14. A method according to claim 13, wherein the imaging capsule provides the measurements of the pressure sensor to the external device to determine the location of the imaging capsule and to instruct the imaging capsule whether to commence or cease scanning the gastrointestinal tract.

15. A method according to claim 11, wherein the imaging capsule includes an encasement made from a rigid material and windows covered by a softer material that is pushed in or pushed out relative to the encasement in response to a difference in pressure inside the imaging capsule and outside the imaging capsule.

16. A method according to claim 15, wherein the rigid material and/or the softer material are penetrable by gas molecules.

17. A method according to claim 11, wherein the imaging capsule is configured to commence scanning upon entering the colon.

18. A method according to claim 11, wherein the imaging capsule is configured to cease scanning upon exiting the colon.

19. A method according to claim 11, wherein the imaging capsule is configured to commence scanning after a preselected amount of time after entering a specific organ.

20. A method according to claim 11, wherein the imaging capsule is configured to scan when identifying the fluctuations or a specific behavior in the pressure measurements.

\* \* \* \* \*